US008000550B2

(12) United States Patent
Yoshida et al.

(10) Patent No.: US 8,000,550 B2
(45) Date of Patent: Aug. 16, 2011

(54) ADAPTIVE DENSITY CORRECTION IN COMPUTED TOMOGRAPHIC IMAGES

(75) Inventors: Hiroyuki Yoshida, Watertown, MA (US); Janne Näppi, Boston, MA (US); Michael E. Zalis, Newtonville, MA (US); Wenli Cai, Dorchester, MA (US)

(73) Assignee: The General Hospital Corporation, Boston, MA (US)

( * ) Notice: Subject to any disclaimer, the term of this patent is extended or adjusted under 35 U.S.C. 154(b) by 974 days.

(21) Appl. No.: 11/606,433

(22) Filed: Nov. 30, 2006

(65) Prior Publication Data

US 2007/0127803 A1    Jun. 7, 2007

Related U.S. Application Data

(60) Provisional application No. 60/741,103, filed on Nov. 30, 2005.

(51) Int. Cl.
*G06K 9/40* (2006.01)
(52) U.S. Cl. ..................... 382/254; 382/131
(58) Field of Classification Search ............ 250/363.04; 345/424; 348/E5.088, E9.042; 378/4–27, 378/82, 87, 901; 382/131, 254
See application file for complete search history.

(56) References Cited

U.S. PATENT DOCUMENTS

| | | | | |
|---|---|---|---|---|
| 5,647,018 | A | * | 7/1997 | Benjamin .................... 382/128 |
| 5,920,319 | A | | 7/1999 | Vining et al. |
| 6,331,116 | B1 | | 12/2001 | Kaufman et al. ............ 434/262 |
| 6,366,800 | B1 | | 4/2002 | Vining et al. |
| 7,226,410 | B2 | | 6/2007 | Long |
| 7,596,256 | B1 | | 9/2009 | Arie et al. |
| 2003/0095695 | A1 | | 5/2003 | Arnold |
| 2004/0114790 | A1 | | 6/2004 | Yamamoto et al. |
| 2004/0167400 | A1 | | 8/2004 | Kaufman |
| 2006/0094961 | A1 | | 5/2006 | Mikheev et al. |
| 2007/0116346 | A1 | * | 5/2007 | Peterson et al. ............ 382/131 |
| 2008/0055308 | A1 | * | 3/2008 | Dekel et al. ................. 345/421 |
| 2008/0273781 | A1 | | 11/2008 | Manduca et al. |

FOREIGN PATENT DOCUMENTS

| | | |
|---|---|---|
| WO | WO 03/034176 | 4/2003 |
| WO | WO 2004/075117 | 9/2004 |
| WO | WO 2005/101314 | 10/2005 |

OTHER PUBLICATIONS

"3D Digital Cleansing Using Segmentation Rays" Proceedings Visualization, Oct. 8, 2000, pp. 37-44.*

(Continued)

*Primary Examiner* — Matthew C Bella
*Assistant Examiner* — Gregory F Cunningham
(74) *Attorney, Agent, or Firm* — Quarles & Brady LLP

(57) ABSTRACT

An adaptive density correction (ADC) method and system automatically compensate for pseudo-enhancement (PEH) of voxels in computed tomography (CT) data, such as in fecal-tagged CT colonography (ftCTC), so air (or another low-contrast background) and soft tissues are represented by their usual CT attenuations. ADC estimates an amount of pseudo-enhancement energy that was received by voxels that are near tagged voxels (i.e., voxels that are tagged with a high-contrast agent), based on a first distribution scheme, such as a Gaussian distribution. ADC then iteratively distributes PEH energy received by voxels to neighboring voxels, according to another distribution scheme, which may be another Gaussian function. ADC then subtracts the total amount of PEH energy at each voxel from the CT data of the voxel.

27 Claims, 13 Drawing Sheets

OTHER PUBLICATIONS

Wenli Cai, et al., "Digital Bowel Cleansing for Computer-Aided Detection for Polyps in Fecal-Tagging CT Colongraphy," *Medical Imaging*, vol. 6144, Mar. 10, 2006, pp. 614422-1-614422-9.

Dongqing Chen, et al., "A Novel Approach to Extract Colon Lumen for CT Images for Virtual Colonoscopy," *IEEE Transactions on Medical Imaging*, vol. 19, No. 12, Dec. 2000, pp. 1220-1226.

Dongqing Chen, et al., "Electronic Colon Cleansing of Colonic Material Tagging and Image Segmentation for Polyp Detection: Detection Model and Method Evaluation," *Nuclear Science Symposium Conference Record*, vol. 3, Oct. 25, 2000, pp. 18131-18125.

Sarong Lakare, et al., "3D Digital Cleansing Using Segmentation Rays," *Proceedings Visualization*, Oct. 8, 2000, pp. 37-44.

Zalis, M., et al., "CT Colonography: Digital Subtraction Bowel Cleansing with Mucosal Reconstruction—Initial Observations," *Radiology*, vol. 226, No. 3, Mar. 2003, pp. 911-917.

Zalis, M., et al., "Digital Subtraction Bowel Cleansing for CT Colonography Using Morphological and Linear Filtration Methods," *IEEE Transactions on Medical Imaging*, Vo. 23, No. 11, Nov. 2004, pp. 1335-1343.

Zigang Wang, et al., "An Improved Electronic Colon Cleansing Method for Detection of Polyps of Virtual Colonoscopy," *Engineering n Medicine and Biology Society*, Sep. 1, 2005, pp. 6512-6515.

International Search Report; Dated Apr. 27, 2007; Rcv'd May 1, 2007; PCT/US2006/045789.

International Search Report; Dated Apr. 27, 2007; Rcv'd May 1, 2007; PCT/US2006/045803.

Authorized Officer Ales Klemencic, *International Preliminary Report on Patentability*; Dated Dec. 27, 2007; PCT/US2006/045789, 11 pages.

Authorized Officer Dorothee Mulhausen, *International Preliminary Report on Patentability*; Dated Jun. 3, 2008; PCT/US2006/045803, 7 pages.

Authorized Officer Ales Klemencic, *International Preliminary Report on Patentability*; Dated Nov. 27, 2007; PCT/US2006/046044, 13 pages.

Article 34 Amendment and Demand, dated Sep. 28, 2007, 25 pages.

Article 34 Amendment and Demand, dated Oct. 2, 2007, 31 pages.

Sethian, "Level Set Methods and Fast Marching Methods", *Cambridge University Press*, 2d edition, ISBN 0521645573, 1999 (Front matter only), 1999, 8 pages.

Frimmel, et al., "Fast and robust method to compute colon centerline in CT colonography," *Proceedings of SPIE*, vol. 5031, 2003, pp. 381-387.

Nappi, et al., "Automated Knowledge-Guided Segmentation of Colonic Walls for Computerized Detection of Polyps in CT Colonography," *Journal of Computer Assisted Tomography*, Jul./Aug. 2002, vol. 26, Issue 4, pp. 493-504.

Frimmel, et al., "Centerline-based colon segmentation for CT colonography," *Med. Phys.*, 32 (8), Jul. 29, 2005, pp. 2665-2672.

Neubauer, Dissertation: Virtual Endoscopy for Preoperative Planning and Training of Endonasal Transsphenoidal Pituitary Surgery, Tu Wien, May 2005.

Singh, et al., Automated 3D Segmentation of the Lung Airway Tree Using Gain-Based Region Growing Approach, MICCAI 2004, LNCS 3217, pp. 975-982, 2004.

United States Patent and Trademark Office, Office Action Summary and Detailed Action, U.S. Appl. No. 11/607,623, Jan. 12, 2010.

United States Patent and Trademark Office, Notice of Allowance, U.S. Appl. No. 11/607,623, Jul. 16, 2010.

United States Patent and Trademark Office, Office Action Summary and Detailed Action, U.S. Appl. No. 11/607,195, Mar. 10, 2010.

United States Patent and Trademark Office, Interview Summary, U.S. Appl. No. 11/607,195, Jun. 14, 2010.

United States Patent and Trademark Office, Notice of Allowance, U.S. Appl. No. 11/607,195, Sep. 28, 2010.

United States Patent and Trademark Office, Office Action Summary and Detailed Action, U.S. Appl. No. 12/832,306, Oct. 1, 2010.

* cited by examiner

- Background, such as air or other gas used to distend colon
- Soft tissue, such as colon wall
- Polyp Key:

Less than -120 HU (generally rendered black)

-120 HU to +100 HU (generally rendered gray)

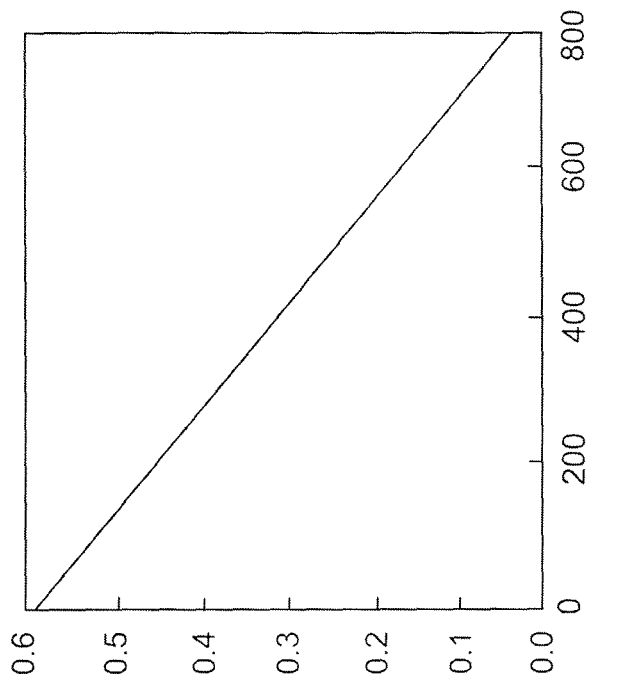
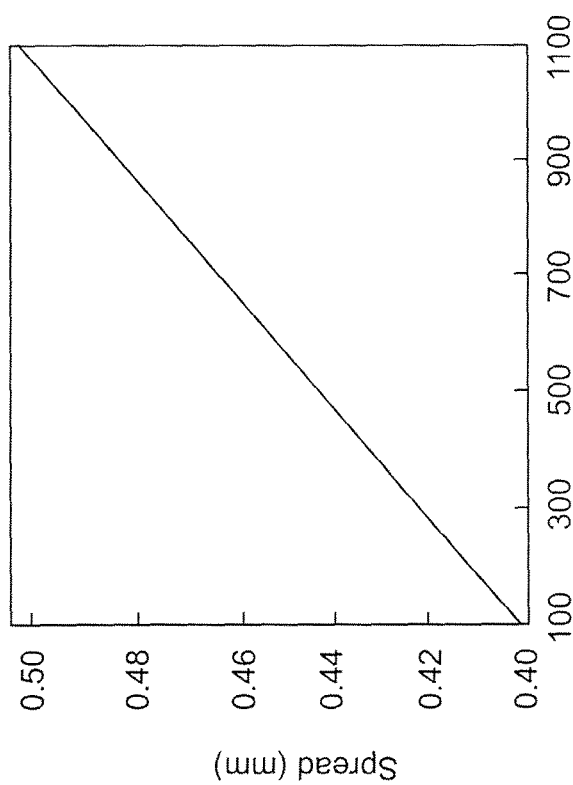
FIG. 9(a)
FIG. 9(b)

ADAPTIVE DENSITY CORRECTION IN COMPUTED TOMOGRAPHIC IMAGES

STATEMENT REGARDING FEDERALLY SPONSORED RESEARCH OR DEVELOPMENT

This invention was made with government support Grant Number CA095279 awarded by the National Cancer Institute. The U.S. Government has certain rights to the invention.

RELATED APPLICATIONS

This application is related to U.S. patent application Ser. No. 11/607,195, titled "Adaptive Density Mapping in Computed Tomographic Images," filed on Nov. 30, 2006, and U.S. patent application Ser. No. 11/607,623, titled "Lumen Tracking in Computed Tomographic Images," filed on Nov. 30, 2006.

BACKGROUND ART

The present invention relates to computed tomography (CT) and, more particularly, to CT systems that reduce the effects of pseudo-enhancement, so air and soft tissues can be represented by their usual CT attenuations.

Colorectal cancer is one of the leading causes of cancer-related deaths. Patient screening can reduce colon cancer by facilitating early detection and removal of pre-cancerous polyps. Colonoscopy is considered to have the highest diagnostic performance for screening colon cancer; however, colonoscopy also has a high cost, risk of complications and incidents of patient non-compliance. A minimally invasive alternative procedure, called computed tomography colonography (CTC) or "virtual colonoscopy," is expected to be more cost effective and to involve a lower risk of complications than traditional colonoscopy.

Proper bowel preparation is considered essential for confident detection of colorectal lesions using CTC. This preparation traditionally includes cathartic cleansing of a patient's colon, because residual material in the colon reduces the sensitivity of CTC by imitating polyps. However, cathartic cleansing usually involves administering a laxative. Such cleansings are uncomfortable for the patient, and some residual material remains in the colon, even after such a cleansing. Orally-administered radio-opaque (or high X-ray opacity) contrast agents, such as dilute barium, can be used to opacify residual fluid and stool, so these opacified ("tagged") materials can be identified and distinguished from polyps or other soft tissues. Procedures that use such tagging are commonly referred to as "fecal tagging CTC" (ftCTC).

Interpreting a large number of ftCTC screening cases can be time-consuming for a radiologist, who may grow weary of the task and occasionally miss small polyps or even subtle cancers. Automated image processing ("computer-aided detection" (CAD)) tools can be used to rapidly point out suspicious lesions to radiologists. However, in ftCTC, automated image processing is complicated by an effect commonly known as pseudo-enhancement (PEH), which is an atrifactual increase in the observed X-ray opacity (radio density) of tissues due to the presence of a near-by high radio density tagging agent.

In computed tomography (CT), the internals of an object, such as a human body, are imaged by taking X-ray measurements, yielding data that represents the object as many tightly packed cubes ("voxels"). The radio density of each voxel is calculated by taking the X-ray measurements through the object from a large number of perspectives. A computer digitally processes the X-ray measurements and generates data that represents a three-dimensional model of the object, including the internals of the object. Essentially, the computer "stacks" a series of "slices" of the object to create the model. The data can then be analyzed by a CAD tool. Alternatively or in addition, the data can be used to generate a three-dimensional display or for some other purpose.

The radio density (also called the "CT attenuation" or "CT number") of each voxel is represented by a numeric value along an arbitrary scale (the Hounsfield scale), in which −1,000 represents the radio density of air, and +1,000 represents the radio density of bone. Air causes very little X-ray attenuation and is typically depicted in black on X-ray films, in CT images, etc., whereas bone greatly attenuates X-rays and is typically depicted in white on these films and images. Fat has a radio density of about −120 Hounsfield Units (HU), and muscle has a radio density of about +40 HU. Water is defined as having a radio density of 0 (zero) HU.

Intermediate amounts of CT attenuation are usually depicted by shades of gray in CT images. Because the human eye is unable to distinguish among 2000 shades of grey (representing HU values between +1,000 and −1,000), a radiographer selects a range of CT attenuations that is of interest (i.e., a range of HU values, known as a "window"), and all the CT attenuations within this range are spread over an available gray scale, such as 256 shades of gray. This mapping of a range of CT attenuations to shades of gray is known as "windowing." The center of the range is known as the "window level." Materials having radio densities higher than the top of the window are depicted in white, whereas materials having radio densities lower than the bottom of the window are depicted in black.

Windowing facilitates distinguishing between tissues having similar radio densities. For example, to image an area of a body, such as the mediastinum or the abdomen, in which many tissues have similar radio densities, a narrow range of CT attenuations is selected, and these CT attenuations are spread over the available shades of gray. Consequently, two tissues with only a small difference between their radio densities are ascribed separate shades of gray and can, therefore, be differentiated.

Soft tissues, including polyps, typically have radio densities of less than 100 HU; however, a near-by tagging agent can pseudo-enhance the measured radio densities of these materials to more than 100 HU, sometimes as high as to 500 HU. Furthermore, the extent of this pseudo-enhancement can vary considerably within a single colon, in part because the amount, thickness and radio density of the tagging agent may vary from place to place within the colon.

This pseudo-enhancement degrades the performance of CAD tools, because these tools use fixed attenuation-based parameters. Thus, in pseudo-enhanced regions, some or all of the voxels that represent a polyp can be misclassified as tagged residual material, due to their high CT attenuations. Consequently, an automatically identified ("extracted") region of the polyp can be significantly smaller than the actual region. In addition, the shape of the region can be severely distorted in the extraction, or the region can be missed entirely. Conventionally-calculated CT attenuation is not, therefore, a reliable feature for automated identification of tagged regions in ftCTC.

SUMMARY OF THE INVENTION

An embodiment of the present invention provides a method for correcting an image value of a voxel p. The method includes calculating an amount of pseudo-enhancement of the voxel p; and reducing an image value of the voxel p by the calculated amount of pseudo-enhancement.

Calculating the amount of pseudo-enhancement may be performed by calculating a pseudo-enhancement energy at a voxel q that neighbors the voxel p; and calculating a portion of the pseudo-enhancement energy received by the voxel p from the voxel q according to a first predetermined distribution scheme. The amount of pseudo-enhancement of the voxel p is related to the amount of pseudo-enhancement energy received by the voxel p.

The first predetermined distribution scheme may include, for example, a Gaussian function, an inverse-square function or an inverse-cube function.

Calculating the pseudo-enhancement energy may include calculating an amount by which an image value, such as a CT attenuation, of the voxel q exceeds a predetermined threshold, such as +100 HU.

Calculating the amount of pseudo-enhancement may optionally include calculating a portion of pseudo-enhancement energy received by the voxel p from a plurality of voxels q, according to the first predetermined distribution function.

Calculating the amount of pseudo-enhancement may further include distributing at least a portion of the pseudo-enhancement energy received by the voxel p to one or more voxels that neighbor the voxel p, according to a second predetermined distribution scheme.

The second predetermined distribution scheme may include, for example, a Gaussian function, an inverse-square function or an inverse-cube function.

Distributing the at least a portion of the pseudo-enhancement energy received by the voxel p to the one or more voxels that neighbor the voxel p may include iteratively distributing the at least a portion of the pseudo-enhancement energy received by the voxel p during an iteration to the one or more voxels that neighbor the voxel p during a subsequent iteration.

The method may include stopping the iterative distribution when a predetermined stopping criteria is satisfied, such as, for example, when an amount of distributable pseudo-enhancement energy is less than about 10 HU or when distributing the at least a portion of the pseudo-enhancement energy would distribute less than about 10 HU.

Another embodiment of the present invention provides a method for compensating for pseudo-enhancement of a voxel in a computed tomography system. The method includes calculating a pseudo-enhancement energy at a voxel q and distributing the calculated pseudo-enhancement energy to one or more voxels p neighboring the voxel q. The method also includes iteratively distributing energy distributed to at least one of the voxels p to at least one voxel neighboring the respective voxel p. The method includes ending the iterative distribution when a predetermined stopping criterion is satisfied and reducing an image value of each voxel p by an amount of energy distributed from the voxel.

The iterative redistribution of residual energy may end when the redistributable energy remaining at the voxel q is less than a predetermined threshold.

Yet another embodiment of the present invention provides a system for correcting an image value of a voxel p. The system includes a computer. The computer is programmed to calculate an amount of pseudo-enhancement of the voxel p and to reduce an image value of the voxel p by the calculated amount of pseudo-enhancement.

Another embodiment of the present invention provides a computer program product. The computer program product includes a computer-readable medium. On the medium is stored computer instructions for calculating an amount of pseudo-enhancement of the voxel p and reducing an image value of the voxel p by the calculated amount of pseudo-enhancement.

BRIEF DESCRIPTION OF THE DRAWINGS

The invention will be more fully understood by referring to the following Detailed Description of Specific Embodiments in conjunction with the Drawings, of which:

FIG. 9 shows two plots of optimized parameter functions of adaptive density correction (ADC) $\sigma_1$ and $\sigma_2$, according to one embodiment of the present invention;

DETAILED DESCRIPTION OF SPECIFIC EMBODIMENTS

The contents of U.S. Provisional Patent Application No. 60/741,103, filed Nov. 30, 2005, titled "A Method for Computer-Aided Detection of Lesions in Radio-Opaque Contrast Materials," is hereby incorporated by reference herein.

In accordance with the present invention, pseudo-enhancement (PEH) of a voxel in computed tomography (CT) data can be automatically compensated by disclosed "adaptive density correction" (ADC) methods and systems. ADC reduces pseudo-enhancement, such as in ftCTC, so air (or another low-contrast background) and soft tissues are represented by their usual CT attenuations. ADC is an iterative process that estimates an amount of pseudo-enhancement that has occurred for certain voxels and subtracts this amount from the CT data of the voxels. ADC then distributes the subtracted amounts to neighboring voxels according to a predetermined scheme, such as a Gaussian distribution.

Figure 1:
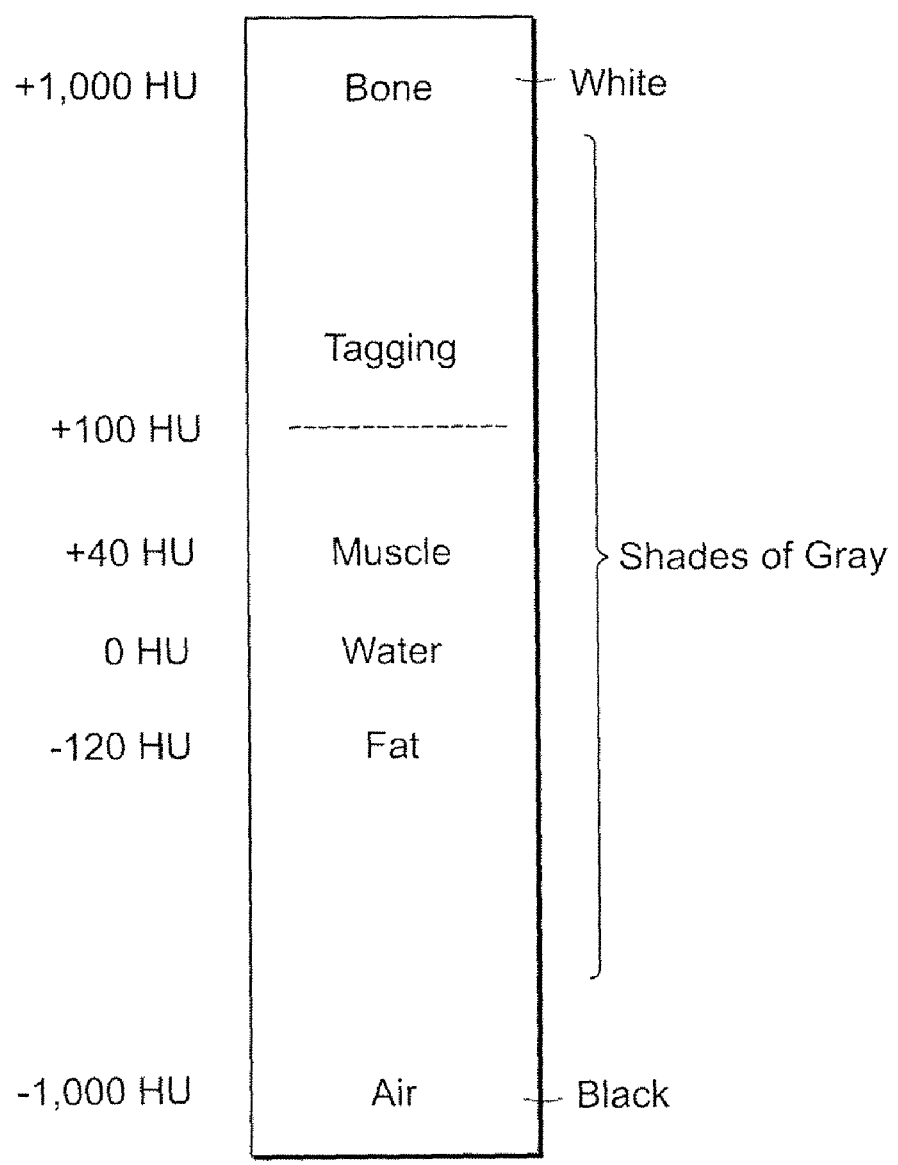
FIG. 1 shows of the Hounsfield scale, along with Hounsfield Unit (HU) values of exemplary materials that may be seen in CT images.
Figure 2:
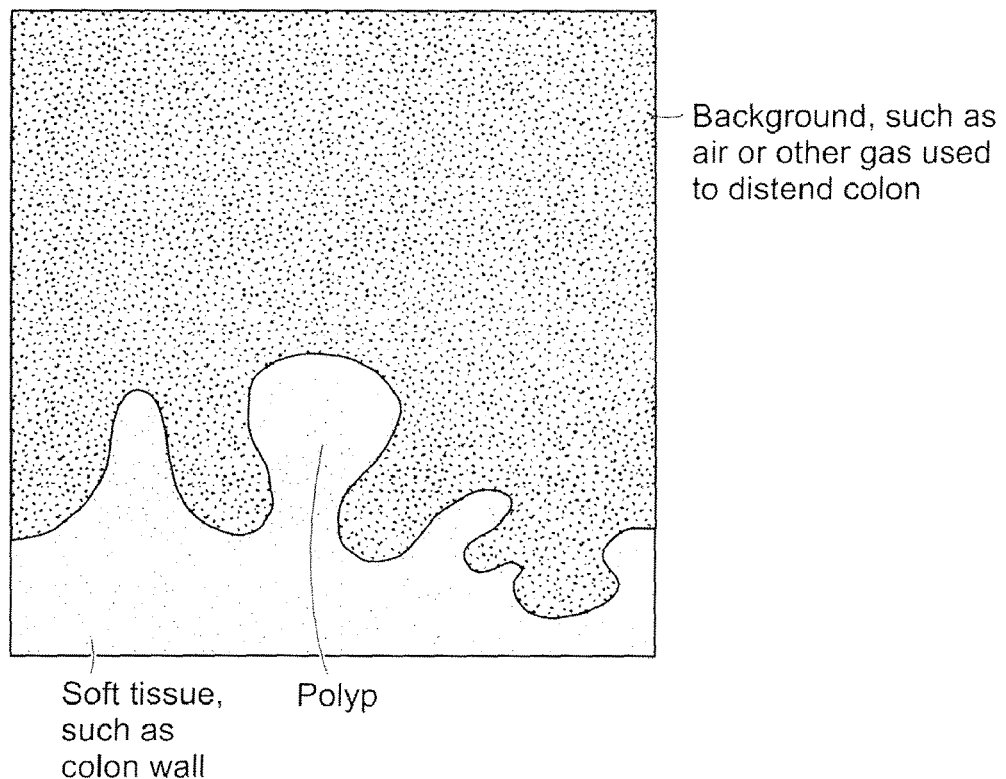
FIG. 2 is an exemplary CT image of a section of a colon that has been cleansed and filled with air or another gas.
Figure 2:
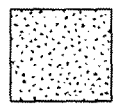
Figure 2:

FIG. 1 shows of the Hounsfield scale, along with HU values of exemplary materials that may be seen in CT images and indications of how these materials may be depicted in the CT images. For example, bone and tagging material are typically depicted in white; muscle, water, fat and other soft tissues are typically depicted in shades of gray; and air is typically depicted in black. FIG. 2 is an exemplary CT image of a section of a colon that has been cleansed and filled with air or another gas. No tagged material is shown in FIG. 2. Soft tissues, such as the colonic wall and a polyp, have CT values between about −120 HU and about +100 HU, whereas the background (air) has a CT value less than about −120 HU.

Figure 3:
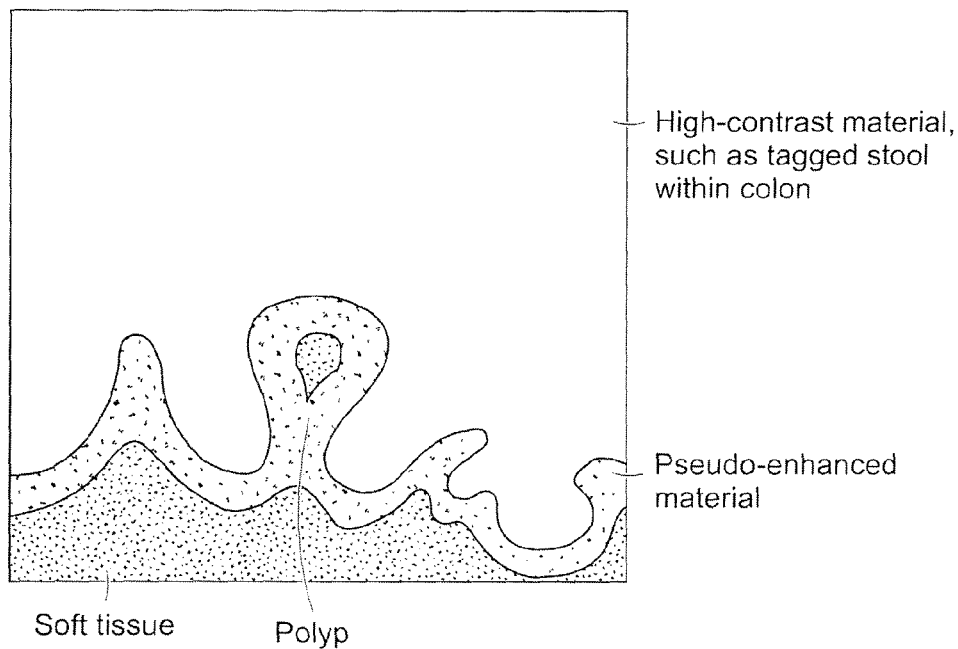
FIG. 3 is an exemplary CT image of a section of a colon that contains tagged fecal material.
Figure 3:
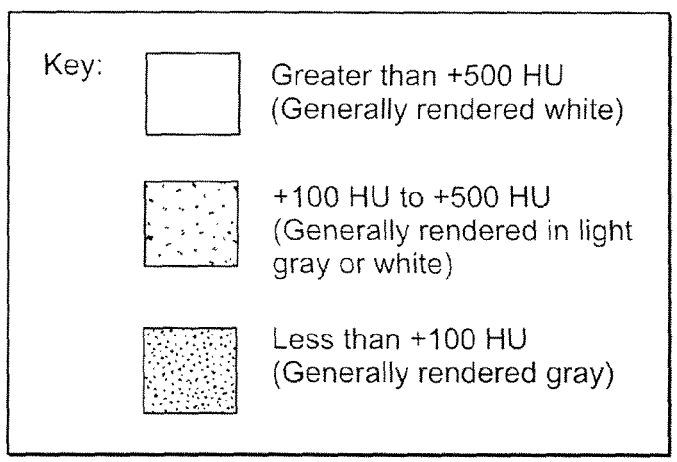

In fecal-tagged CT colonography, opacified residual material can imitate polyps, and pseudo-enhancement can artificially increase the radio density of neighboring soft tissue. For example, FIG. 3 is an exemplary CT image of a section of a colon that contains tagged fecal material. The high radio density tagging artificially increases the observed density of neighboring soft tissue, i.e., the neighboring soft tissue is pseudo-enhanced, resulting in a fuzzy boundary between the soft tissue and the background, as well as distortion of the polyp and a decrease in the polyp size (volume).

Figure 4:
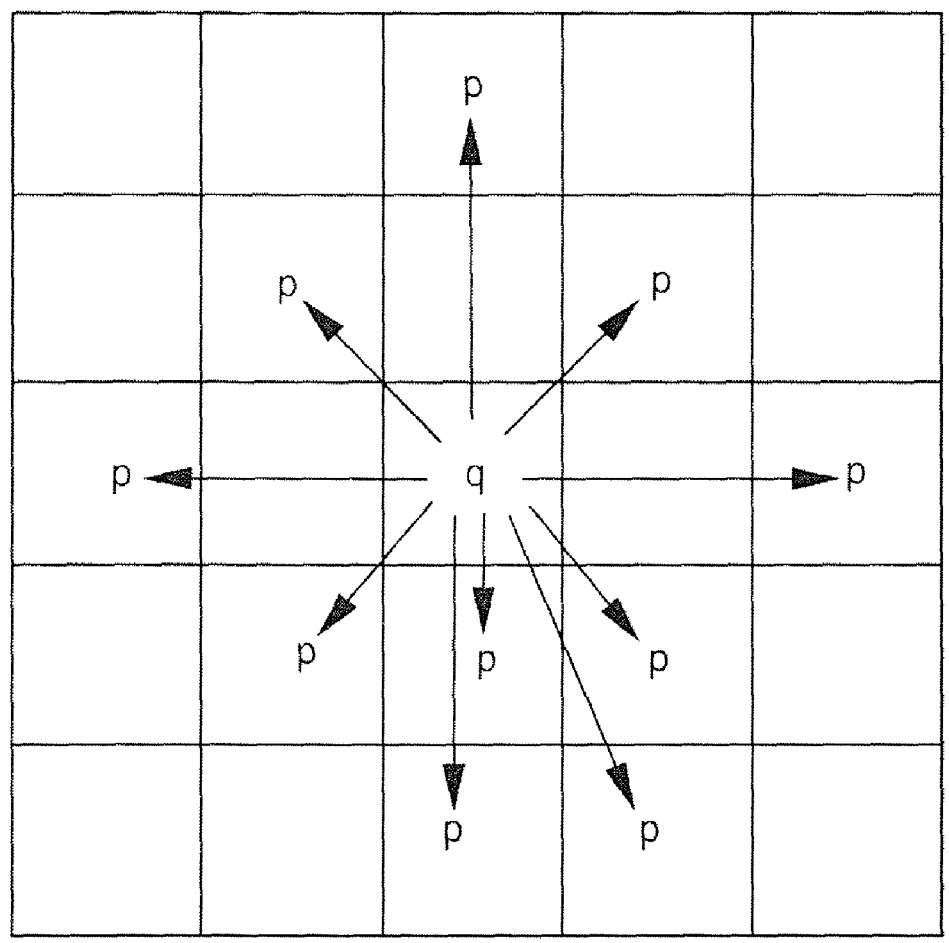
FIG. 4 is a schematic diagram of several voxels, including a voxel q that can cause pseudo-enhancement of one or more other voxels p.
Figure 5:
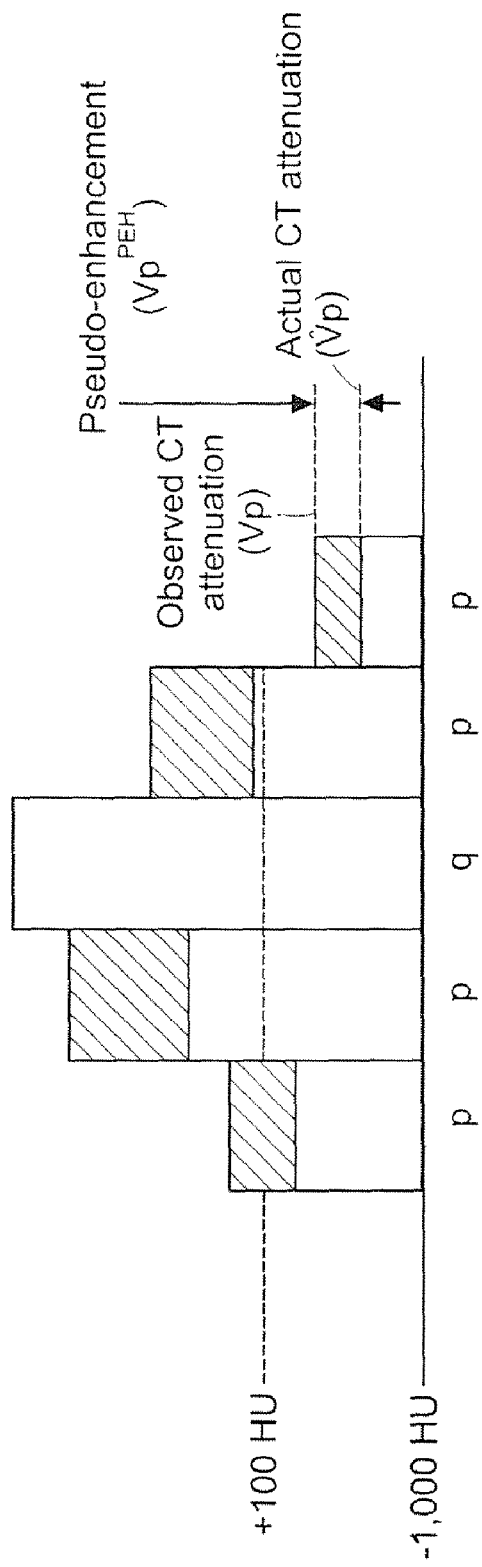
FIG. 5 is a bar graph depicting exemplary observed CT attenuations for several voxels p, exemplary actual CT attenuations for the voxels p, as well as exemplary amounts of pseudo-enhancement experienced by the voxels, according to one embodiment of the present invention.

As shown in FIG. 4, tagged material in a voxel q can cause pseudo-enhancement of one or more voxels p that are near (i.e., that neighbor) voxel q. It should be noted that "neighbor" voxels need not be directly next to each other, i.e., there may be intervening voxels between neighbor voxels. (For simplicity, FIG. 4 does not show all the voxels p that may be pseudo-enhanced by the voxel q. In addition, FIG. 4 is a 2-dimensional representation, although pseudo-enhancement typically occurs in three dimensions.) Exemplary amounts of pseudo-enhancement ($v_p^{PEH}$) experienced by several voxels p, as a result of being near voxel q, are depicted in a bar graph in FIG. 5. FIG. 5 also shows exemplary observed CT attenuations ($v_p$) and exemplary actual CT attenuations ($\hat{v}_p$) for the voxels p.

Figure 6:
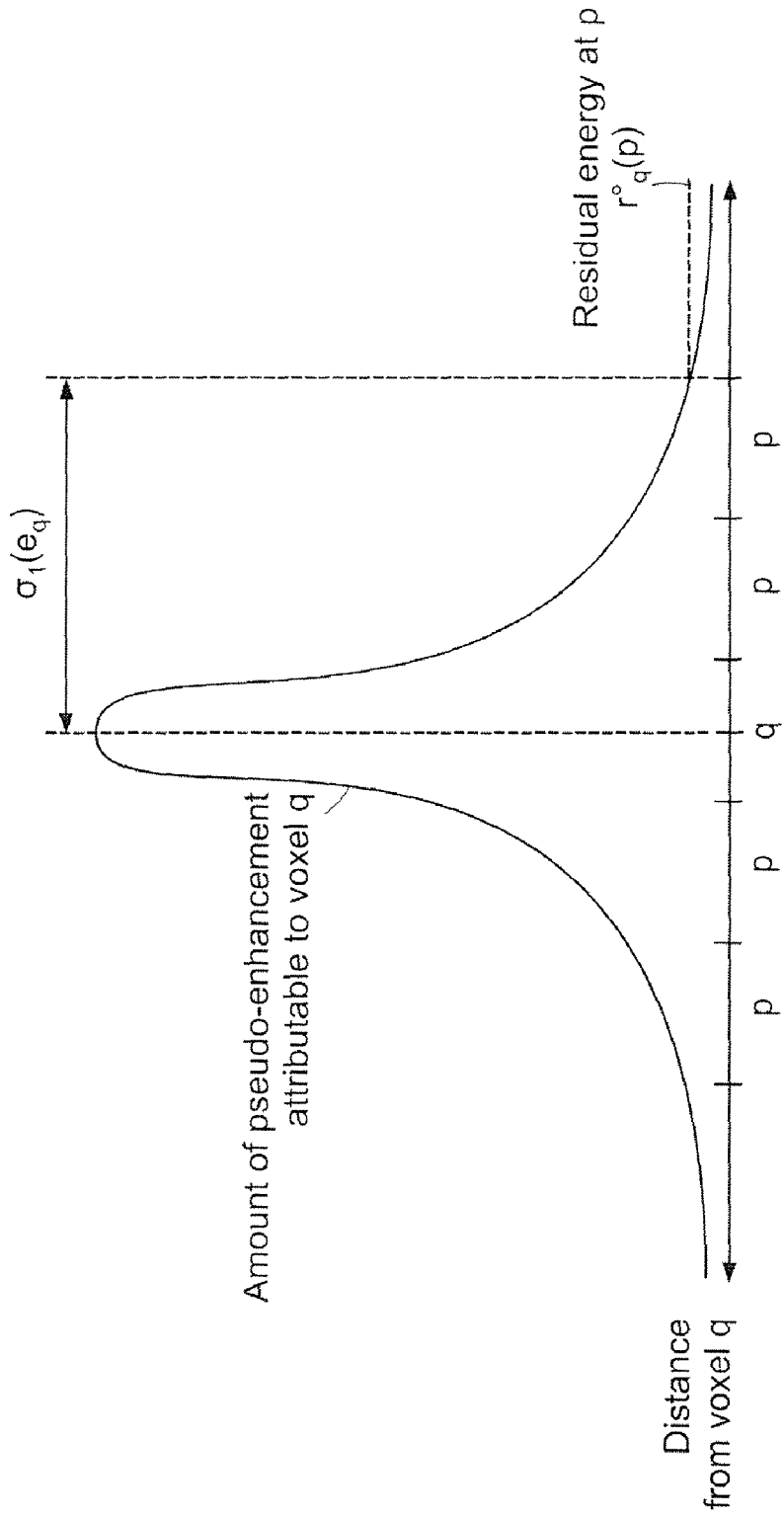
FIG. 6 is a graph that depicts exemplary amounts of pseudo-enhancement experienced by several voxels p, according to one embodiment of the present invention.

The amount of pseudo-enhancement varies with distance from the voxel q, such as according to a Gaussian function $\sigma_1$. FIG. 6 depicts amounts of pseudo-enhancement experienced by several voxels p, which is attributable to voxel q, according to an exemplary Gaussian function. Other functions, such as inverse-square (for two dimensions) and inverse-cube (for three dimensions) can be used to model the distribution of PEH.

Figure 7:
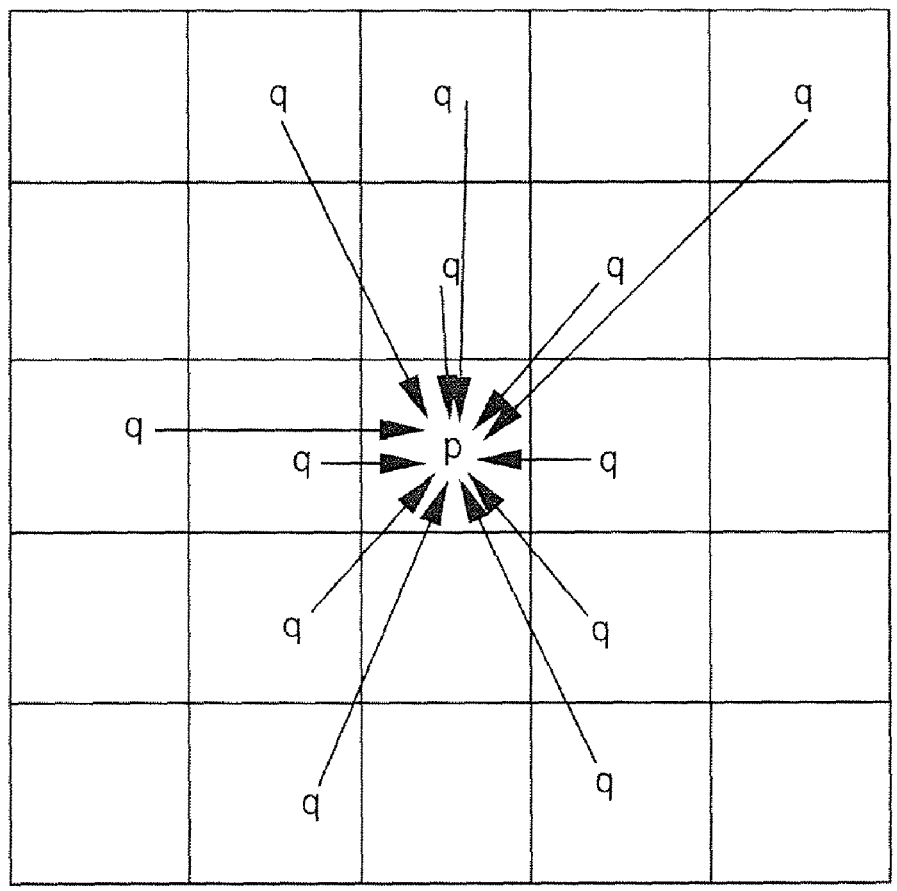
FIG. 7 is a schematic diagram of several voxels, including a voxel p that can be pseudo-enhanced by several other voxels q.

Each voxel p can be pseudo-enhanced by one or more near-by voxels q. Furthermore, each voxel p can be pseudo-enhanced by voxels that contain tagged material and/or voxels that do not necessarily contain tagged material, but that have been pseudo-enhanced by one or more other voxels. Thus, the PEH experienced by one voxel p can be a cumulative result of PEH from many voxels q, as depicted in FIG. 7.

The PEH of a voxel p can be corrected in several stages. First, an amount of PEH produced by a tagged voxel q is estimated. This amount of PEH is assumed to have been distributed to neighboring voxels p, as described above. This "first order pseudo-enhancement energy" received by the voxels p is subtracted from the observed CT values for the voxels p.

Next, because pseudo-enhanced voxels can pseudo-enhance other voxels, "higher order" scattering from pseudo-enhanced voxels is estimated. This amount of PEH is also assume to have been distributed to neighboring voxels according to another Gaussian function ($\sigma_2$) or another suitable distribution function. This high order PEH energy received is also subtracted from the observed CT values for the voxels.

Figure 8:
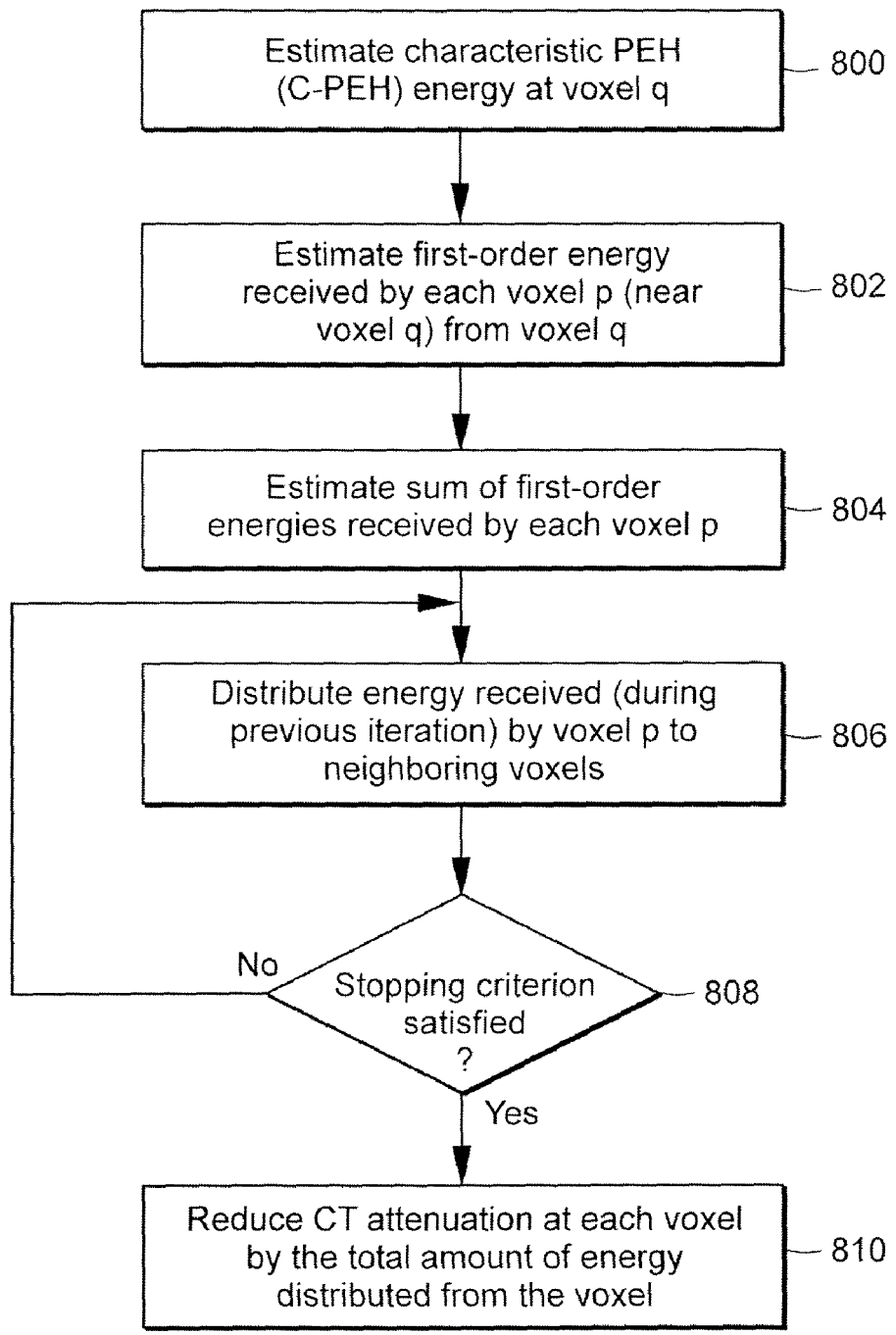
FIG. 8 is a flowchart depicting operations performed to compensate for pseudo-enhancement, according to one embodiment of the present invention.
Figure 10A:
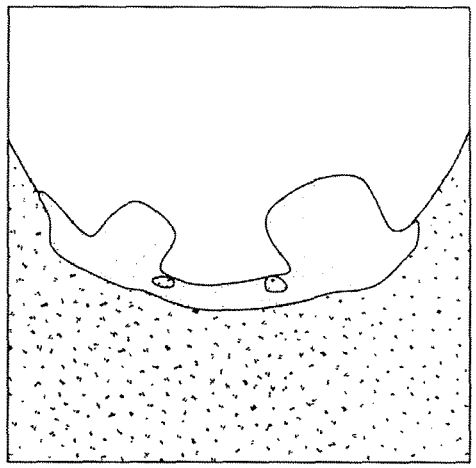
FIG. 10 shows an example of the application of optimized ADC to a phantom filled with a high-density 900-HU tagging solution.
Figure 10B:
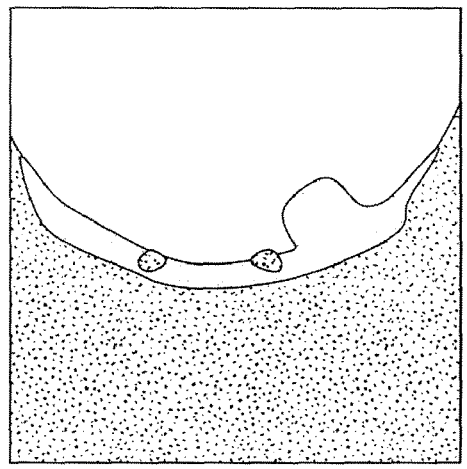
Figure 10C:
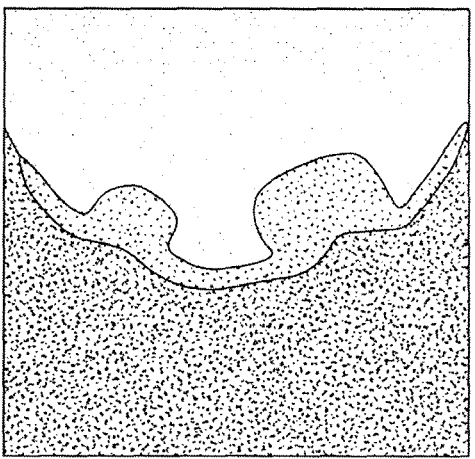
Figure 10D:
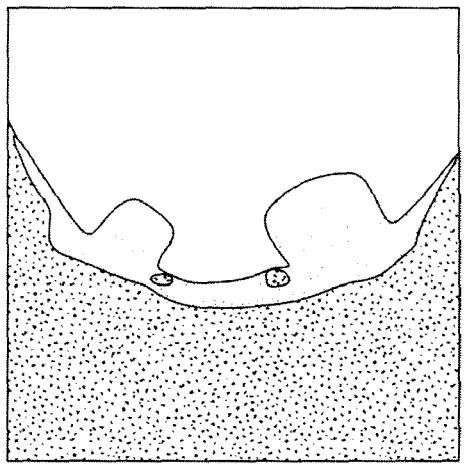
Figure 11A:
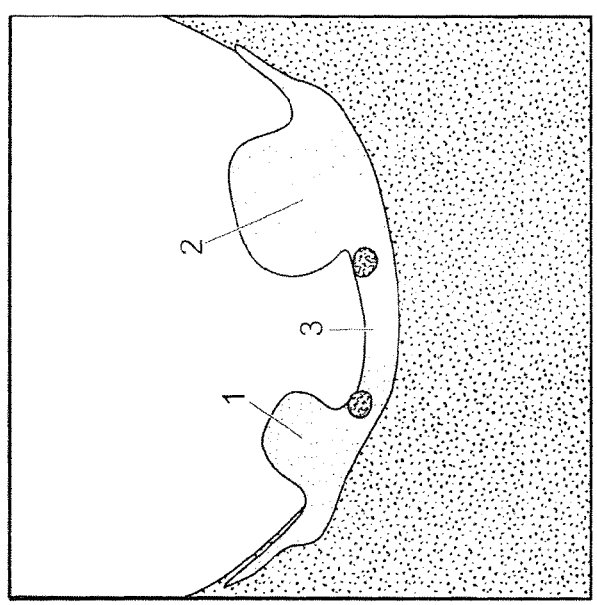
FIG. 11 shows profile plots of simulated polyps and a wall without and with ADC, according to one embodiment of the present invention.
Figure 11B:
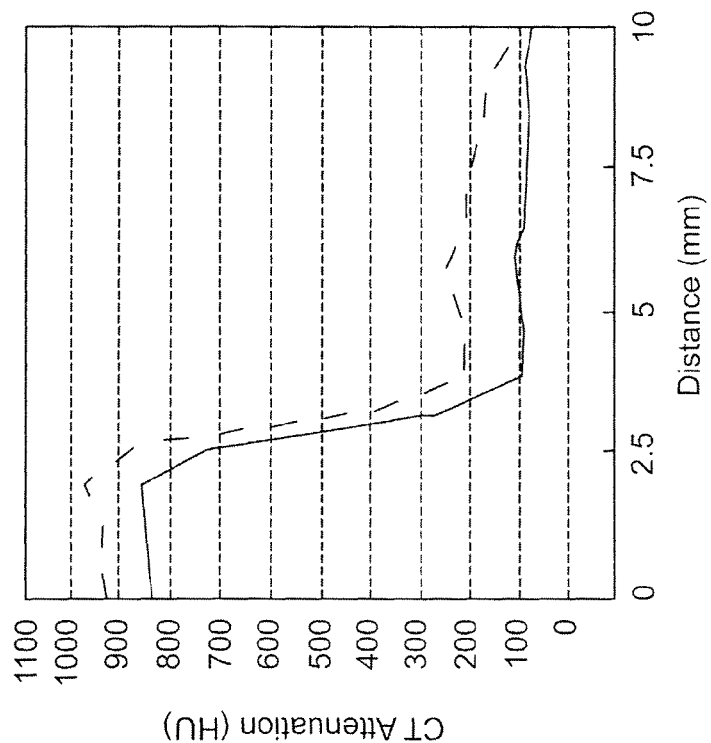
Figure 11D:
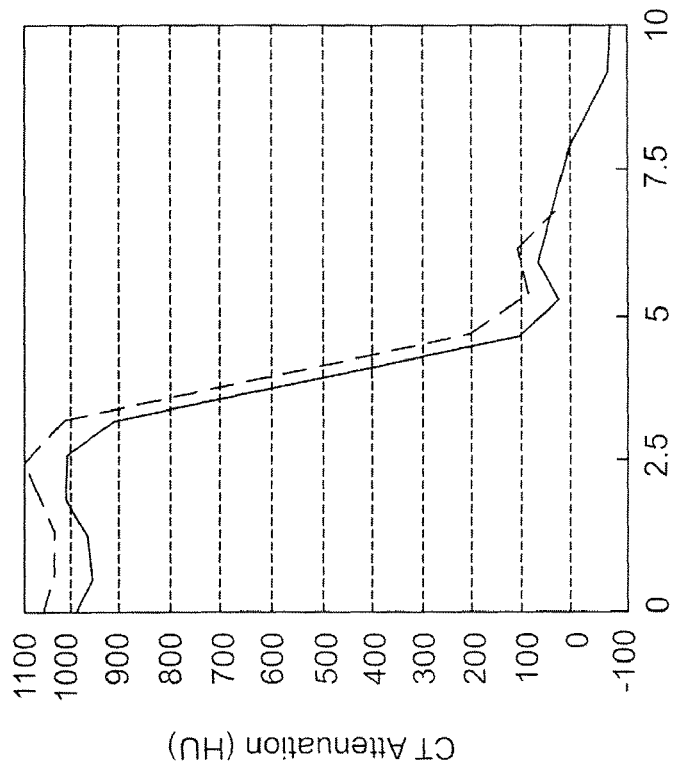
Figure 11C:
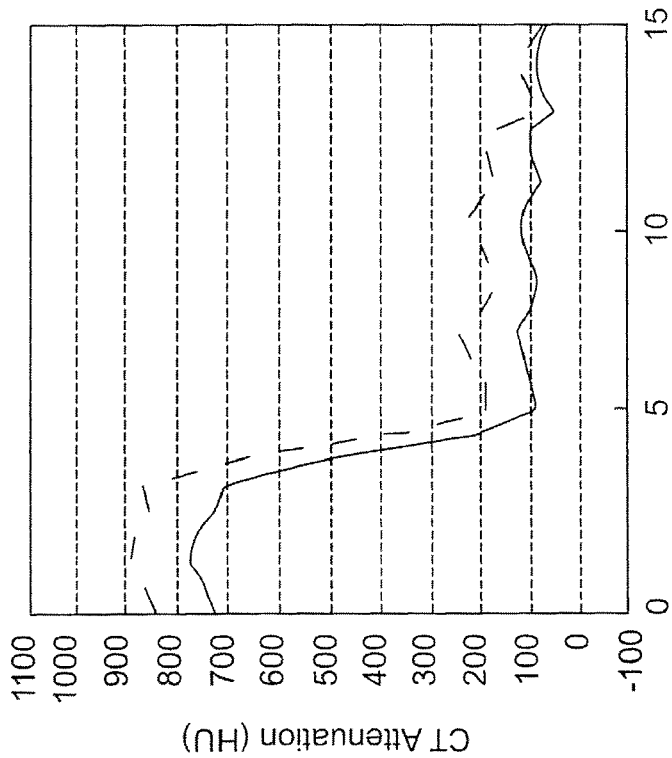
Figure 12A:
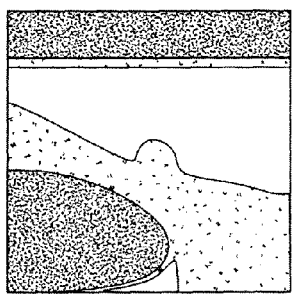
FIG. 12 shows examples of the application of ADC to two clinical cases, in accordance with one embodiment of the present invention.
Figure 12B:
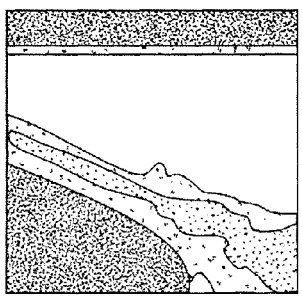
Figure 12C:
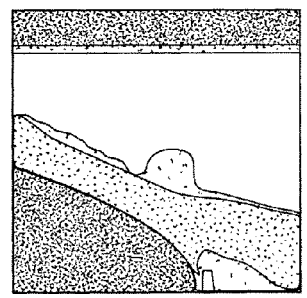
Figure 12D:
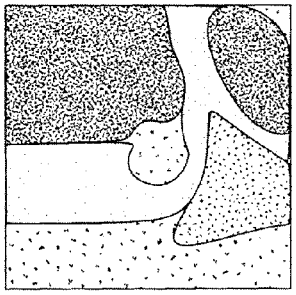
Figure 12E:
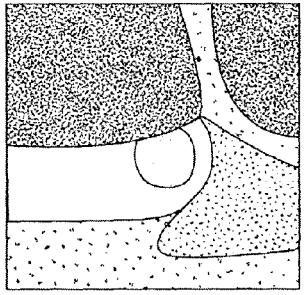
Figure 12F:
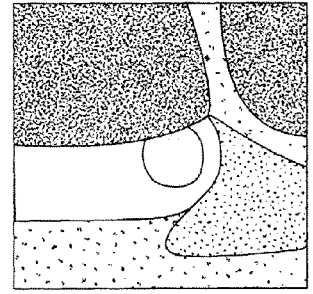

By this mechanism, PEH energy is "distributed" or "redistributed" (collectively hereinafter "distributed") among the voxels. This distribution is preferably performed iteratively, until a predetermined stopping criterion is reached. This process is summarized in a flowchart shown in FIG. 8. At 800, a characteristic pseudo-enhancement (C-PEH) energy is estimated for a voxel q. A first-order energy received by each voxel p (near the voxel q) from the voxel q is estimated at 802. It should be noted that the C-PEH is calculated for many voxels q. A sum of the first-order energies received by each voxel p is estimated, as shown at 804.

After the first-order energy from the voxels q is distributed to the voxels p, the energy received by each voxel is iteratively distributed to neighboring voxels. During each iteration, energy received by each voxel p during the previous iteration is distributed to voxels that are near the voxel p, as shown at 806. This iteration continues until a predetermined stopping criterion is satisfied, as shown at 808. After the iteration is complete, the CT attenuation of each voxel is reduced by the amount of energy that was distributed from the voxel, as shown at 810. Exemplary formulae, calculations and algorithms for estimating PEH energy and for distributing this energy are described in detail below.

Exemplary Formulae, Calculations and Algorithms

In CT imaging, a three-dimensional (3-D) representation of a target volume is reconstructed from measurements integrated along various paths of X-ray probe radiation. The relationship between the X-ray field function $f$ and its projection along the different paths $s_i$ through the target volume at a specific time instant can be expressed as $$\int_{S_i} f(x,y,z)ds = \Phi_i(\rho_i, \theta, z), \tag{1}$$

where $\Phi_i$ denotes the measured value, $f$ is the spatial field function, $\rho_i$ is the in-plane coordinate of the projection, $\theta$ is the transillumination angle and z is the height of a cross-sectional plane in the target volume.

The attenuation of a monochromatic X-ray can be modeled as $$I = I_0 \exp(-\mu(x,y,z)s) + I_0 S, \tag{2}$$

where $I_0$ is the transmitted X-ray intensity, I is the observed X-ray intensity, $\mu$ is a spatially varying absorption coefficient that depends on the physical properties of the target material and the wavelength of the radiation, s is the irradiation path length and S is the fraction of scattered radiation. By including the attenuation model in Eq. (1), the measured projection can be expressed as $$\log_e(I/I_0) = -\int_{S_i} \mu(x,y,z)ds. \tag{3}$$

The scattering of the X-rays is caused by the physical interactions of the X-rays with the target volume, and it becomes more dominant as the physical density of the target material increases. Therefore, in ftCTC, the introduction of high-density tagging not only opacifies residual materials, but it also introduces PEH in nearby materials. It has been estimated that for each 1 mg/ml of administered (iodinated) tagging agent, the observed CT attenuation, which models the underlying physical density of the target material, increases by 25 HU.

The X-ray scattering is not the only image-degrading factor in CT imaging. For example, CT measurements also tend to be distorted by a partial-volume effect (PVE) that results from the finite sampling of the target volume. The PVE effect at a voxel with CT attenuation v can be modeled as $$v = \sum_i c_i \times v_i, \quad (4)$$

where the terms $v_i$ represent the CT attenuations of the materials affecting the voxel, and the terms $c_i$ are the corresponding partial-volume elements with $\Sigma_i c_i = 1$.

Optimal modeling and correction for the various image-degrading effects within ftCTC data would require access to the original CT projection data, the reconstruction algorithms and the CT scan parameters. Unfortunately, in CTC, end users do not have access to these data. Instead, they are provided with a set of transverse (axial) slices reconstructed from the original CT scan data by use of proprietary algorithms. Furthermore, it is not clear how faithfully the original physical volume is represented by the reconstruction algorithms. Therefore, to maximize the scope of the application of the disclosed correction method for CTC, ADC may be implemented as a post-processing method that approximates the observed PEH effects in the output data of a CT scanner. ADC is a general-purpose image processing method that minimizes the effects of PEH on any input CTC data. Embodiments of ADC are described in the context of a fully automated CAD scheme for detecting colorectal polyps. However, ADC can also be used in other contexts, such as detecting pre-cancerous materials in other parts of a body, as well as in non-cancer related studies and studies that involve inanimate objects.

ADC is based upon three basic observations of the perceived effect of the PEH on transverse CTC slices. First, the PEH originates from voxels $\{p_T\}$ representing tagged regions with high CT attenuation. Second, the magnitude of the effect of PEH increases with increasing CT attenuation of the voxels $\{p_T\}$. Third, the effect of PEH decreases with increasing distance from the voxels $\{p_T\}$.

We modeled the PEH as an iterative model that approximates the above effects as an energy distribution originating from high-density regions in CT data. The energy from X-ray scatter elevates CT attenuation at voxels that receive the distributed energy. Let $v_p$ denote the observed CT attenuation at a voxel p, and let $\hat{v}_p$ denote the actual CT attenuation of p without the effect of PEH. Then, the observed CT attenuation of p can be represented as $$v_p = \hat{v}_p + v_p^{PEH}, \quad (5)$$

where the additive term $v_p^{PEH}$ represents the PEH at p, approximating the collective summation of the effects of scatter and PVE from the neighboring voxels. Thus, we can minimize the effect of PEH at p by subtracting the estimated $v_p^{PEH}$ from the observed CT attenuation of p.

To estimate $v_p^{PEH}$, we first calculate a "characteristic pseudo-enhancement" (C-PEH) energy at q by $$e_q = \begin{cases} v_q - \tau_q, & \text{if } v_q > \tau_q \quad (6) \\ 0, & \text{otherwise} \quad (7) \end{cases}$$

where $\tau_q \in R$ is a thresholding parameter. The C-PEH energy models the distributed energy from X-ray scatter based upon the observed density of the target material; the distributed energy is distributed to the neighboring voxels of p according to a Gaussian function. We use Gaussian functions, because they provide a good collective approximation for various effects of imaging noise in the model, and because they provide a separable kernel for computational efficiency. However, other functions, such as inverse square or inverse cube functions, can also be used to distribute this energy. The first-order pseudo-enhancement energy received at a voxel p from the voxel q≠p is represented by $$r_q^0(p) = \frac{e_q}{\sqrt{2\pi \sigma_1(v_q)}} \exp\left(-\frac{1}{2}\left(\frac{D(p,q)}{\sigma_1(v_q)}\right)^2\right), \quad (8)$$

where $\sigma_1(v_q)$ determines the Gaussian spread of the energy as a function of the observed CT attenuation of q, and D(q,p) indicates a distance between voxels q and p. Thus, the total first-order energy received by p from voxels q is represented by $$r^0(p) = \sum_q r_q^0(p). \quad (9)$$

In practice, the energy received from voxels far away from p is negligible, and we can implement Eq. (9) simply by distributing the local energy calculated at voxels q cumulatively to their neighboring voxels within $1+\text{Ceiling}(2\sigma_1(v_q))$ voxels from q.

Next, we simulate the effects of higher-order scatter by distributing (redistributing) the total energy received at voxel p in Eq. (9) iteratively to the voxels that neighbor voxel p. These iterations account for the perceived cumulative widening of the region affected by the PEH as the observed CT attenuations within a high-density region become higher. At each iteration, only the residual energy received during the previous iterations is redistributed, i.e., at iteration $n \geq 1$, the energy redistributed by a voxel p is $r^{n-1}(p)$. Thus, the total residual energy received by p at iteration n can be obtained from Eqs. (8) and (9) as $$r^n(p) = \sum_q \frac{r^{n-1}(q)}{\sqrt{2\pi} \, \sigma_2(r^{n-1}(q))} \exp\left(-\frac{1}{2}\left(\frac{D(p,q)}{\sigma_2(r^{n-1}(q))}\right)^2\right), \quad (10)$$

where $\sigma_2(r^{n-1}(q))$ represents the Gaussian spread of the redistributed residual energy at q. Here again, other distribution functions, such as inverse square or inverse cube, can be used. The iteration over Eq. (10) terminates when the redistributable energy becomes negligible, as discussed in detail below.

We estimate the effect of PEH at p as a sum of the total distributed energy that includes the first- and higher-order effects; therefore, the actual CT attenuation of p can be approximated by $$\hat{v}_p = v_p - v_p^{PEH} \approx v_p - \sum_{i=0}^n r^i(p). \quad (11)$$

To implement the ADC method, we use a global threshold value, $\tau_q = 100$ HU, for all voxels q in the CTC data in Eq. (6). Although the ADC method can be implemented in arbitrary-dimensional Euclidean space, including 3-D CT volumes, we computed the effect of PEH only by use of in-plane voxels to reduce computation time, thereby assuming that the PEH effects between transverse CT slices can be considered to be negligible. The latter simplification is based on the observation that the distortion of CTC data by metallic artifacts has a limited effect in the transverse direction, even if severe in-plane distortion is observed. Therefore, for the Euclidian distance between two voxels, p and q, in Eqs. (8) and (10), D(p,q) is represented by $\sqrt{(x_p-x_q)^2+(y_p-y_q)^2}$, where $(x_p,y_p)$ and $(x_q,y_q)$ are the in-plane coordinates of voxels p and q, respectively. The iteration over Eq. (10) is terminated when the additive effect of the remaining redistributable energy becomes less than 10 HU, although other stopping criteria can be used. For example, the stopping criterion can be more than 10 HU, such as 20 HU, or less than 10 HU, such as 5 HU. In another example, the iteration is terminated when the additive effect of the remaining redistributable energy becomes less than a predetermined fraction, such as 5%, of the energy in voxel p or q.

Parameter Estimation

The ADC method requires the estimation of two spread functions, $\sigma_1$ and $\sigma_2$ in Eqs. (8) and (10), respectively. The first function models the magnitude of the first-order pseudo-enhancement energy from the observed CT attenuation values, and the second function models the higher-order scatter effects from the distributed residual energy. These functions can be approximated as linear functions:

$$\sigma_1(x)=ax+b, \sigma_2(x)=cx+d. \quad (12)$$

Linear functions were used because the precise form of the spread functions is not obvious, and because they facilitate fast optimization of the ADC. Other approximations or exact formulas or values can be used.

The optimization of the ADC was performed by use of a brute-force optimization algorithm with simultaneous application of the same ADC model to multiple CTC datasets. Let $\gamma_j(V_k), j \in \{1, \ldots, N\}$, represent the soft-tissue regions of interest (ROIs) in the j-th CTC dataset after application of the ADC to the N datasets with a parameter vector $V_k=(a_k,b_k,c_k,d_k)$, where $k \geq 1$ indicates an iteration index. Let $u_{j,k}$ represent the maximum observed CT attenuation value in $mma_j(V_k)$, i.e., $$u_{j,k}=\max\{v_p; p \in \gamma_j(V_k)\}. \quad (13)$$

The objective function that should be minimized during the optimization is $$f(V_k)=(u_{1,k}, \ldots, u_{N,k}). \quad (14)$$

Suppose that $V_k$ provides the minimum value of $f$ at the k-th iteration. Then the next parameter set, $V_{k+1}=(a_{k+1},b_{k+1},c_{k+1},d_{k+1})$, is chosen to satisfy $$50 \leq u_{j,k+1} \leq u_{j,k}, \forall j \in \{1, \ldots, N\}. \quad (15)$$

We used an anthropomorphic human-colon phantom (available from Phantom Laboratory, Salem, N.Y.) as the CTC dataset in the above optimization process. The materials of the phantom were designed to resemble features observed in human CTC scans. In particular, the simulated soft-tissue materials had CT attenuations <100 HU, and the simulated polyps had an average CT attenuation of 50 HU.

To estimate the effect of PEH on soft-tissue materials for various tagging regimens, we filled the phantom partially with three different concentrations of Oxilan (available from Guerbet, Bloomington, Ind.), and we scanned the phantom by use of a four-channel CT scanner (model Lightspeed, available from GE Medical Systems, Milwaukee, Wis.). The CT parameters were similar to those used routinely for clinical cases at the Massachusetts General Hospital: 3.75 mm collimation, a 1.8 mm reconstruction interval, a of current of 50 mA and a voltage of 140 kVp. The three resulting CT scans represented the phantom with uniform taggings of retained fluid at 300 HU, 600 HU, and 900 HU. As expected, the perceived effect of PEH was low at 300 HU, moderate at 600 HU, and high at 900 HU. For example, at 300 HU, the CT attenuation of untagged regions was elevated only in the immediate vicinity of tagged fluid, and the observed increment was small (<50 HU). At 900 HU, the CT attenuations of untagged regions could be elevated over wide regions with increments of >500 HU.

We extracted the same 80×80×80-mm ROI from the three CT scans by use of a semi-automated method and assigned them as $\gamma_j, j \in 1,2,3$. The use of an ROI, rather than the complete phantom, facilitated fast sampling of a homogeneous region of the underlying materials for the time-consuming brute-force optimization of the method. The selected ROI included regions of air, tagged fluid, the colonic wall and five simulated polyps $\geq 8$ mm. The results of the optimization are described next.

Results

FIG. 9 shows two plots of the optimized parameter functions of the ADC, (a) $\sigma_1$ and (b) $\sigma_2$, optimized as described above. In FIG. 9a, the plot of $\sigma_1$ indicates that voxels with high observed CT attenuation have their C-PEH energy distributed over a wider region than do voxels with low CT attenuation. In FIG. 9b, the plot of $\sigma_2$ indicates that, during an iteration step, high residual energies are distributed over a smaller region than low residual energies. Although this may seem counter-intuitive, it should be noted that high residual energies are distributed effectively over several iterations, decreasing to a lower energy level at each iteration, whereas low residual energies have a negligible effect after the first iteration. Thus, despite the declining slope of $\sigma_2$, high residual energies indeed do affect a wider region than do low energies.

FIG. 10 shows an example of the application of the optimized ADC to a phantom filled with a high-density 900-HU tagging solution. FIGS. 10a and 10b show 8-mm and 12-mm pseudo-enhanced polyps with lung display (range: [−1,000, 600] HU) and soft-tissue display (range: [−200, 200] HU) windows, respectively. The PEH distortion of the polyps is particularly noticeable with the soft-tissue display window, shown in FIG. 10b. The total PEH energy, $v_p^{PEH}$, estimated by the ADC, is depicted in FIG. 10c. Bright regions indicate high energies, and dark regions indicate low energies. As expected, the largest PEH correction occurs in the vicinity of the voxels with the highest CT attenuations, and the smallest correction occurs outside the colonic lumen. FIG. 10d shows the result of the application of ADC with a soft-tissue display window. Most of the pseudo-enhanced CT attenuations have been restored to the soft-tissue range, and the perceived shapes of the polyps demonstrate significantly less distortion than do those of FIG. 10b.

FIG. 11 shows profile plots of the simulated polyps and wall without and with ADC. FIG. 11a indicates the sampled locations, and FIGS. 11b, 11c, and 11d demonstrate the reduction in the CT attenuation values by ADC. FIG. 11b shows a profile plot of the smaller polyp; FIG. 11c shows a profile plot of the larger polyp; and FIG. 11d shows a profile plot of the wall region. The dotted and solid curves show the profile plots before and after the application of the ADC, respectively. As expected, the CT attenuation values are lower after the application of ADC. In each case, ADC has reduced the CT attenuation values within the simulated soft-tissue region to the range of 100 HU.

FIG. 12 shows examples of the application of ADC to two clinical cases. The top row displays a small 6-mm polyp subjected to severe PEH due to being covered by high-density (800 HU) tagging. In FIGS. 12a and 12b, the polyp is shown with lung display and soft-tissue display windows, respectively. Severe distortion by PEH is evident. In FIG. 12c, the result of the ADC is shown with a soft-tissue display window. The ADC has recovered most of the region of the polyp. The bottom row of FIG. 12 displays a 10-mm polyp covered by low-density (200 HU) tagging. In FIGS. 12d and 12e, the region is shown with lung display and soft-tissue display windows, respectively. The effect of the pseudo-enhancement is negligible, due to the low density of the tagging agent. Because of the low CT attenuation of the surrounding region, ADC has a negligible effect on the region, as can be seen in FIG. 12f, which demonstrates the result of the ADC in the soft-tissue display window.

A system for implementing the above-described adaptive density correction may be implemented by a computer executing instructions stored in a memory. Input data, such as CT values of voxels in a CT scan of a human being, can be provided from a CT system to the above-described computer, or the above-described computer can be integrated into the CT system. In common practice, CT data is received from a CT system and stored in a picture archiving and communication system (PACS). This data can be used by the above-described computer to perform ADC, such as in a preprocessing step prior to CAD.

Some of the functions performed by the ADC system and method have been described with reference to flowcharts. Those skilled in the art should readily appreciate that functions, operations, decisions, etc. of all or a portion of each block, or a combination of blocks, of the flowcharts can be implemented as computer program instructions, software, hardware, firmware or combinations thereof. Those skilled in the art should also readily appreciate that instructions or programs defining the functions of the present invention can be delivered to a processor in many forms, including, but not limited to, information permanently stored on non-writable storage media (e.g. read only memory devices within a computer, such as ROM, or devices readable by a computer I/O attachment, such as CD-ROM disks), information alterably stored on writable storage media (e.g. floppy disks and hard drives) or information conveyed to a computer through communication media, including computer networks. In addition, while the invention may be embodied in software, the functions necessary to implement the invention may alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Moreover, while the preferred embodiments are described in connection with CT data, one skilled in the art will recognize that the system may be embodied using data from a variety of image systems, such as magnetic resonance imaging (MRI), X-ray, ultrasound and the like. Furthermore, subsets, combinations and subcombinations of the described systems and methods can be used alone or with other systems. Accordingly, the invention should not be viewed as limited, except by the scope and spirit of the appended claims.

What is claimed is:

1. A method for correcting an image value of a voxel p, comprising:
    calculating an amount of pseudo-enhancement of the voxel p;
    reducing an image value of the voxel p by the calculated amount of pseudo-enhancement;
    wherein calculating the amount of pseudo enhancement comprises:
        calculating a pseudo-enhancement energy at a voxel q that neighbors the voxel p; and
        calculating a portion of the pseudo-enhancement energy received by the voxel p from the voxel q according to a first predetermined distribution scheme;
    wherein the amount of pseudo-enhancement of the voxel p is related to the amount of pseudo-enhancement energy received by the voxel p.

2. A method as defined in claim 1, wherein the first predetermined distribution scheme comprises a Gaussian function.

3. A method as defined in claim 1, wherein the first predetermined distribution scheme comprises an inverse-square function.

4. A method as defined in claim 1, wherein the first predetermined distribution scheme comprises an inverse-cube function.

5. A method as defined in claim 1, wherein calculating the pseudo-enhancement energy comprises calculating an amount by which an image value of the voxel q exceeds a predetermined threshold.

6. A method as defined in claim 5, wherein the image value is a CT attenuation and the predetermined threshold is about +100 HU.

7. A method as defined in claim 1, wherein calculating the amount of pseudo-enhancement further comprises:
    calculating a portion of pseudo-enhancement energy received by the voxel p from a plurality of voxels q, according to the first predetermined distribution function.

8. A method as defined in claim 1, wherein calculating the amount of pseudo-enhancement further comprises:
    distributing at least a portion of the pseudo-enhancement energy received by the voxel p to one or more voxels that neighbor the voxel p, according to a second predetermined distribution scheme.

9. A method as defined in claim 8, wherein the second predetermined distribution scheme comprises a Gaussian function.

10. A method as defined in claim 8, wherein the second predetermined distribution scheme comprises an inverse-square function.

11. A method as defined in claim 8, wherein the second predetermined distribution scheme comprises an inverse-cube function.

12. A method as defined in claim 8, wherein distributing the at least a portion of the pseudo-enhancement energy received by the voxel p to the one or more voxels that neighbor the voxel p comprises:
    iteratively distributing the at least a portion of the pseudo-enhancement energy received by the voxel p during an iteration to the one or more voxels that neighbor the voxel p during a subsequent iteration.

13. A method as defined in claim 12, further comprising:
    stopping the iterative distribution when a predetermined stopping criteria is satisfied.

14. A method as defined in claim 12, further comprising:
stopping the iterative distribution when an amount of distributable pseudo-enhancement energy is less than about 10 HU.

15. A method as defined in claim 12, further comprising:
stopping the iterative distribution when distributing the at least a portion of the pseudo-enhancement energy would distribute less than about 10 HU.

16. A method for compensating for pseudo-enhancement of a voxel in a computed tomography system, the method comprising:
calculating a pseudo-enhancement energy at a voxel q;
distributing the calculated pseudo-enhancement energy to one or more voxels p neighboring the voxel q;
iteratively distributing energy distributed to at least one of the voxels p to at least one voxel neighboring the respective voxel p;
ending the iterative distribution when a predetermined stopping criterion is satisfied; and
reducing an image value of each voxel p by an amount of energy distributed from the voxel p.

17. A method as defined in claim 16, wherein ending the iterative redistribution of residual energy when the redistributable energy remaining at the voxel q is less than a predetermined threshold.

18. A system for correcting an image value of a voxel p in an image, comprising:
a computer programmed to access the image and calculate an amount of pseudo-enhancement of the voxel p corresponding to an artificial increase in an observed opacity of tissues represented in the voxel p; and
reduce an image value of the voxel p by the calculated amount of pseudo-enhancement.

19. A computer program product, comprising:
a non-transitory computer-readable medium on which is stored computer instructions for:
calculating an amount of an artificial increase in an observable opacity of tissues represented in a voxel p due to the presence of a high radio density tagging agent in proximity to tissues represented in the voxel p; and
reducing an image value of the voxel p by the calculated amount artificial increase in the observable opacity of tissues represented in a voxel p.

20. The system as defined in claim 18, wherein to calculate the amount of pseudo enhancement the computer is programmed to:
calculating a pseudo-enhancement energy at a voxel q that neighbors the voxel p; and
calculating a portion of the pseudo-enhancement energy received by the voxel p from the voxel q according to a first predetermined distribution scheme;
wherein the amount of pseudo-enhancement of the voxel p is related to the amount of pseudo-enhancement energy received by the voxel p.

21. The system as defined in claim 18, wherein calculating the amount of pseudo-enhancement further comprises calculating a portion of pseudo-enhancement energy received by the voxel p from a plurality of voxels q that neighbor voxel p, according to the first predetermined distribution function.

22. The system as defined in claim 18, wherein calculating the amount of pseudo-enhancement further comprises distributing at least a portion of the pseudo-enhancement energy received by the voxel p to one or more voxels that neighbor the voxel p, according to a second predetermined distribution scheme.

23. The system as defined in claim 22, wherein distributing the at least a portion of the pseudo-enhancement energy received by the voxel p to the one or more voxels that neighbor the voxel p comprises:
iteratively distributing the at least a portion of the pseudo-enhancement energy received by the voxel p during an iteration to the one or more voxels that neighbor the voxel p during a subsequent iteration.

24. The computer program product as defined in claim 19, wherein the stored computer instructions for calculating the amount of artificial increase in the observable opacity of tissues represented in the voxel p includes:
calculating an amount of artificial increase in the observable opacity of tissues represented in a voxel q that neighbors the voxel p; and
calculating a portion of the amount of artificial increase in the observable opacity of tissues received by the voxel p from the voxel q according to a first predetermined distribution scheme;
wherein the amount of artificial increase in the observable opacity of tissues of the voxel p is related to the amount of artificial increase in the observable opacity of tissues received by the voxel p.

25. The computer program product as defined in claim 19, wherein calculating the amount of artificial increase in the observable opacity of tissues comprises calculating a portion of artificial increase in the observable opacity of tissues received by the voxel p from a plurality of voxels q that neighbor voxel p, according to the first predetermined distribution function.

26. The computer program product as defined in claim 19, wherein calculating the amount of artificial increase in the observable opacity of tissues t further comprises distributing at least a portion of the artificial increase in the observable opacity of tissues received by the voxel p to one or more voxels that neighbor the voxel p, according to a second predetermined distribution scheme.

27. The computer program product as defined in claim 19, wherein distributing the at least a portion of the artificial increase in the observable opacity of tissues received by the voxel p to the one or more voxels that neighbor the voxel p comprises:
iteratively distributing the at least a portion of the artificial increase in the observable opacity of tissues received by the voxel p during an iteration to the one or more voxels that neighbor the voxel p during a subsequent iteration.

\* \* \* \* \*